(12) United States Patent
Smith et al.

(10) Patent No.: US 11,618,919 B2
(45) Date of Patent: Apr. 4, 2023

(54) ULTRASENSITIVE MICRO RNA QUANTIFICATION

(71) Applicant: The Board of Trustees of the University of Illinois, Urbana, IL (US)

(72) Inventors: Andrew Smith, Savoy, IL (US); Lucas David Smith, Monticello, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 201 days.

(21) Appl. No.: 16/881,619

(22) Filed: May 22, 2020

(65) Prior Publication Data
US 2020/0407783 A1  Dec. 31, 2020

Related U.S. Application Data

(60) Provisional application No. 62/851,826, filed on May 23, 2019.

(51) Int. Cl.
*C12Q 1/6851* (2018.01)

(52) U.S. Cl.
CPC ..... *C12Q 1/6851* (2013.01); *C12Q 2525/207* (2013.01); *C12Q 2531/125* (2013.01); *C12Q 2537/155* (2013.01); *C12Q 2561/12* (2013.01); *C12Q 2565/626* (2013.01); *C12Q 2565/629* (2013.01)

(58) Field of Classification Search
CPC ............ C12Q 1/6851; C12Q 2525/207; C12Q 2531/125; C12Q 2537/155; C12Q 2561/12; C12Q 2565/626; C12Q 2565/629
See application file for complete search history.

(56) References Cited

U.S. PATENT DOCUMENTS

| | | | | |
|---|---|---|---|---|
| 2007/0111257 A1* | 5/2007 | Kohne | ................... | G01N 33/68 435/7.1 |
| 2016/0253584 A1* | 9/2016 | Fodor | .................. | C12Q 1/6813 235/494 |
| 2018/0100180 A1* | 4/2018 | Lin | ...................... | C12Q 1/6816 |

OTHER PUBLICATIONS

Eugene Berezikov, "Evolution of microRNA diversity and regulation in animals", Nature Reviews|Genetics, vol. 12, Dec. 2011, doi: 10.1038/nrg3079.
Choi et al., "Next-Generation in Situ Gybridization Chain Reaction: Higher Gain, Lower Cost, Greater Durability", American Chemical Society, vol. 8, No. 5, 4284-4294, 2014.
Chou et al., "miRTarBase update 2018: a resource for experimentally validated microRNA-target interactions", Nucleic Acids Research, 2018, vol. 46, doi: 10.1093/nar/gkx1067.
Dragan et al., "SYBR Green I: Fluorescence Properties and Interaction with DNA", J Fluoresc, 2012, 22: 1189-1199.
Gadkar et al., "A novel method to perform genomic walks using a combination of single strand DNA circulatization and rolling circle amplification", Journal of Microbiological Methods 87 (2011) 38-43.
Gebert et al., "Regulation of microRNA function in animals", Nature Reviews, Molecular Cell Biology, vol. 20, Jan. 2019, 17 pages.
He et al., "Current State of Circulating MicroRNAs as Cancer Biomarkers", Clinical Chemistry 61:9, 1138-1155 (2015).
Huang et al., "Exosomal miR-1290 and miR-375 as Prognostic Markers in Castration-resistant Prostate Cancer", European Urology 67 (2015) 33-41.
Huang et al., "High-throughput optical sensing of nucleic acids in a nanopore array", Nature Nanotechnology, vol. 10, Nov. 2015, 7 pages.
Hunt et al., "MicroRNA Detection: Current Technology and Research Strategies", Annual Rev. Anal. Chem. 2015, 8, 217-237.
Johnson-Buck et al., "Kinetic fingerprinting to identify and count single nucleic acids", Nature Biotechnology, vol. 33, No. 7, Jul. 2015, 4 pages.
Keller et al., "Toward the blood-borne miRNome of human diseases", Nature Methods, vol. 8, No. 10, Oct. 2011, 5 pages.
Krutzik et al., "Fluorescent Cell Barcoding for Multiplex Flow Cytometry", Curr Protoc Cytom. Jan. 2011, Chapter: Unit—6.31, 22 pages.
Larsson et al., "In situ detgection and genotyping of individual mRNA molecules", Nature Methods, vol. 7, No. 5, May 2010, 6 pages.
Liang et al., "Characterization of microRNA expression profiles in normal human tissues", BMC Genomics 2007, 8:166, 21 pages.
Mage et al., "Shape-based separation of synthetic microparticles", Nature Materials, vol. 18, Jan. 2019, 82-89.
Mitchell et al., "Circulating microRNAs as stable blood-based markers for cancer detection", PNAS, Jul. 29, 2008, vol. 105, No. 30, 10513-10518.
Rouhanifard et al., "ClampFISH detects individual nucleic acid molecules using click chemistry-based amplification", Nature Biotechnology, vol. 37, No. 1, Jan. 2019, 11 pages.
Serge et al., "Dynamic multiple-target tracing to probe spatiotemporal cartograhy of cell membranes", Nature Methods, vol. 5, No. 8, Aug. 2008, 8 pages.
Shikha et al., "Versatile design and synthesis of nano-barcodes", Chem Soc Rev., 2017, 46, 7054, 40 pages.
Skog et al., "Glioblastoma microvesicles transport RNA and proteins that promote tumour growth and provide diagnostic biomarkers", Nature Cell Biology, vol. 10, No. 12, Dec. 2008, 12 pages.
Smith et al., "High-Fidelity Single Molecule Quantification in a Flow Cytometer Using Multiparametric Optical Analysis", ACS Nano 2020, 14, 2324-2335.
Tavallaie et al., "Nucleic acid hybridization on an electrically reconfigurable network of gold-coated magnetic nanoparticles enables microRNA detection in blood", Nature Nanotechnology, vol. 13, Nov. 2018, 1066-1071.

(Continued)

*Primary Examiner* — David C Thomas
(74) *Attorney, Agent, or Firm* — Dilworth IP, LLC

(57) ABSTRACT

The present invention relates to an ultrasensitive assay platform for the detection of nucleic acids such as microRNAs (miRNAs), which are important biomarker for diseases including cancer. The platform allows high throughput detection of multiple nucleic acid sequences miRNAs on the single-molecule level using fluorescence labeling, molecular barcoding, and flow based detection and multiparametric data analysis.

16 Claims, 11 Drawing Sheets

Specification includes a Sequence Listing.

(56) References Cited

OTHER PUBLICATIONS

Tuma et al., "Characterization of SYBR Gold Nucleic Acid Gel Stain: A Dye Optimized for Uses with 300-nm Ultraviolet Transilluminators", Analytical Biochemistry 268, 278-288, 1999.
Ullal et al., "Cancer cell profiling by barcoding allows multiplexed protein analysis in fine needle aspirates", Sci Transl Med. Jan. 15, 2014, 6, 219, 22 pages.
Van Der Pol et al., "Particle size distribution of exosomes and microvesicles determined by transmission electron microscopy, flow cytometry, nanoparticle tracking analysis, and resistive pulse sensing", Journal of Thrombosis and Haemostasis, 12, 1182-1192, 2014.
Vitzthum et al., "A Quantitative Fluorescence-Based Microplate Assay for the Determination of Double-Stranded DNA Using SYBR Green I and a Standard Ultraviolet Transilluminator Gel Imaging System", Analytical Biochemistry 276, 59-64, 1999.
Wang et al., "miR-375 induces docetaxel resistance in prostate cancer by targeting SEC23A and YAP1", Molecular Cancer 2016, 15:70, 11 pages.
Weisstein Website, "Ball Picking", printed Nov. 19, 2021, 1 page.
Kenneth W. Witwer, "Circulating MicroRNA Biomarker Studies: Pitfalls and Potential Solutions", Clinical Chemistry 61:1, 56-63, 2015.
Zhou et al., "Phage-mediated counting by the naked eye of miRNA molecules at attomolar concentrations in a Petri dish", Nature Materials, vol. 14, Oct. 2015, 8 pages.

\* cited by examiner

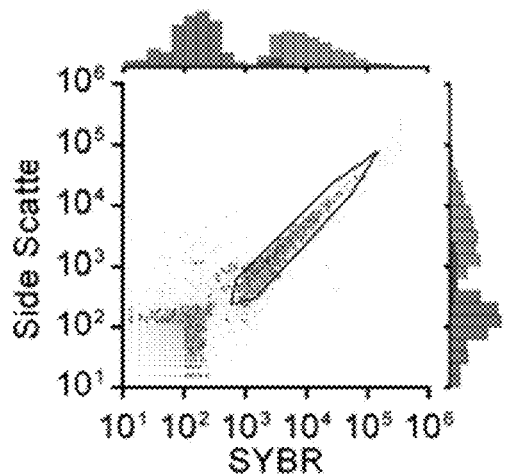
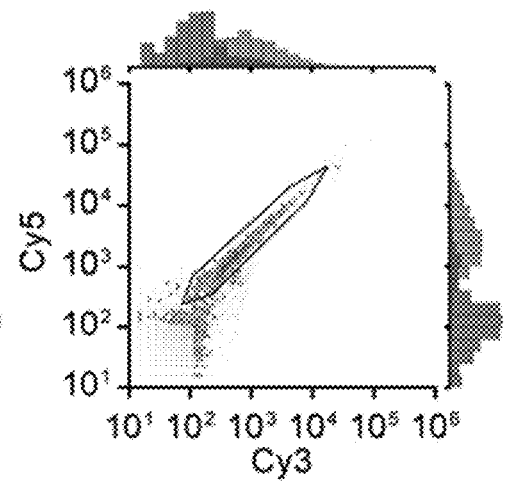
Fig. 4A Fig. 4B
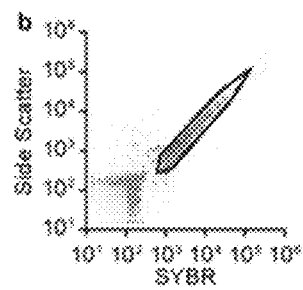
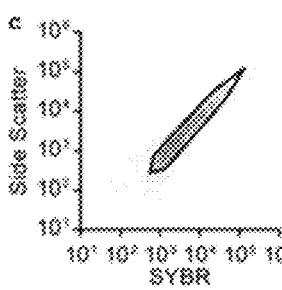
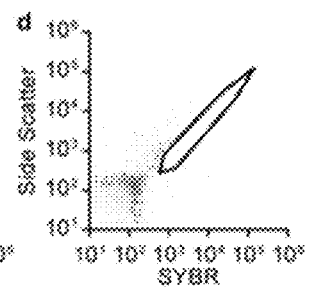
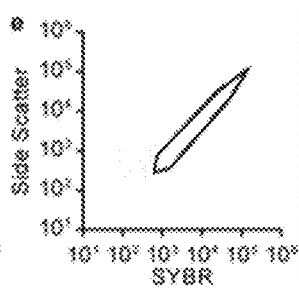
Fig. 5B Fig. 5C Fig. 5D Fig. 5E
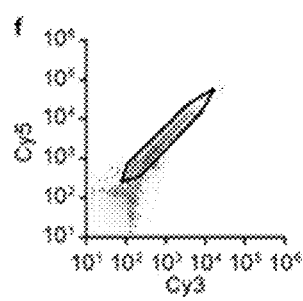
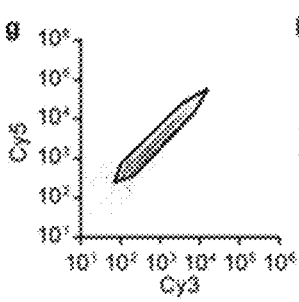
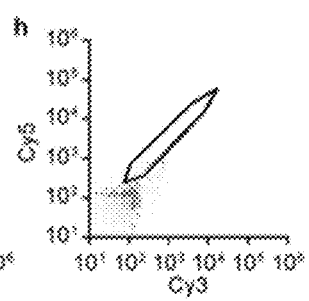
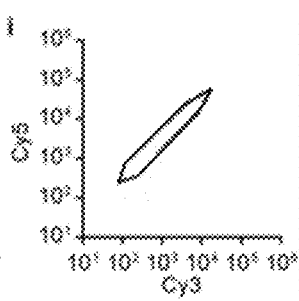
Fig. 5F Fig. 5G Fig. 5H Fig. 5I

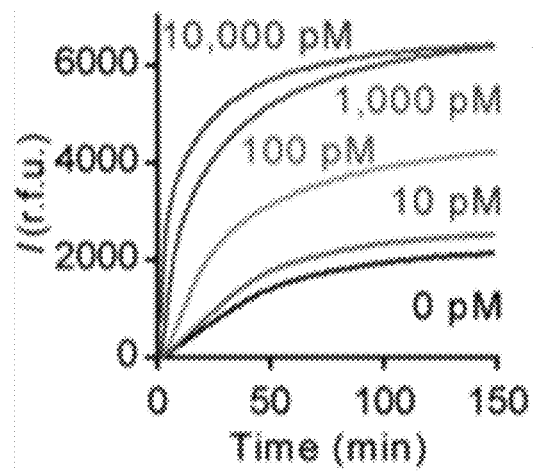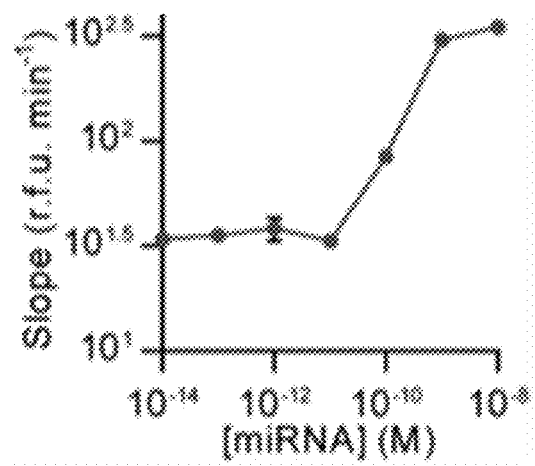
Fig. 7A
Fig. 7B
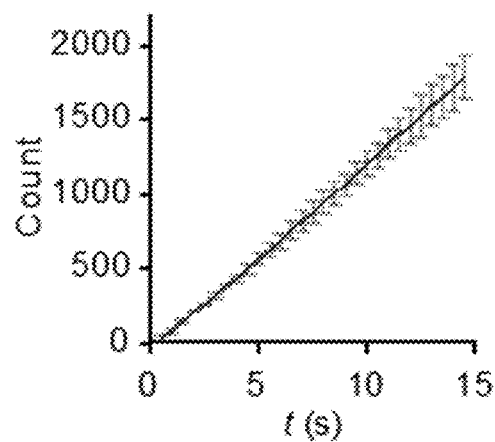
Fig. 7C

SEQUENCE LISTING

```
<160> NUMBER OF SEQ ID NOS: 10

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uuuguucguu cggcucgcgu ga                                                  22

<210> SEQ ID NO 2
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phosphate group

<400> SEQUENCE: 2
caacaaccaa caaacacaga atgctcacgc gagccgaacg aacaaacctc agcaacacca         60
aacaacaaac                                                                70

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Alexa Fluor 405 dye

<400> SEQUENCE: 3
cctcagcaac acc                                                            13

<210> SEQ ID NO 4
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' dibenzocyclooctyne

<400> SEQUENCE: 4
actttacttt actttacttt actttacttt acttttacttt actttactt actttacttt         60 actttactca cgcgagccga acgaacaaa                                           89
```

```
<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Alexa Fluor 430 dye

<400> SEQUENCE: 5
cctcagcaac acc                                                          13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Cy3 dye

<400> SEQUENCE: 6
cctcagcaac acc                                                          13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Alexa Fluor 594 dye

<400> SEQUENCE: 7
cctcagcaac acc                                                          13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Cy5 dye

<400> SEQUENCE: 8
cctcagcaac acc                                                          13

<210> SEQ ID NO 9
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Cy5 dye

<400> SEQUENCE: 9
acacagaatg ct                                                           12

<210> SEQ ID NO 10
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: 5' Alexa Fluor 700 dye

<400> SEQUENCE: 10
cctcagcaac acc                                                              13
```

ULTRASENSITIVE MICRO RNA QUANTIFICATION

STATEMENT REGARDING FEDERALLY SPONSORED RESEARCH

This invention was made with government support under Grant No. NIH 1 R01 CA227699-01 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 27, 2020, is named 128-018US_SL.txt and is 3,119 bytes in size.

FIELD OF THE INVENTION

The present invention provides an ultrasensitive assay platform for the detection of ribonucleic acids on the single molecule level, for example, the detection of small nucleic acids, the most common of which are microRNAs, also known as miRNAs, miRs, or micro ribonucleic acids, known to be important biomarkers for diseases including cancers. The present method counts microRNAs, and other ribonucleic acids, at the single molecule level using flow cytometry after DNA extension and dense labeling with e.g., sequence specific fluorophore conjugated dye-DNA hybridization probes, incorporation of fluorescently labeled nucleotides into the extended DNA, and the like. The platform of the invention allows high throughput detection and quantification of miRNAs across four orders of magnitude of concentration, and allows miRNAs to be spectrally barcoded for multiplexed detection of multiple distinct miRNA sequences.

BACKGROUND OF THE INVENTION

Interest in microRNAs (miRNAs) has been driven by their discovery as ubiquitous cell regulatory factors and disease biomarkers, however, miRNA quantification remains challenging. MicroRNAs are short non-coding RNAs present in nearly all mammalian cells that regulate gene expression by transcript silencing[1,2]. Interest by the clinical community in these endogenous molecules has grown considerably due to the recent discovery they are detectable in a wide range of bodily fluids and that their concentrations correlate with a variety of disease states.[3-6] However, consistent and accurate quantification of short nucleic acids, in particular miRNA, remains a major challenge[8-8a]. Next-Generation Sequencing (NGS) provides an absolute readout of all sequences present, but its low throughput capacity and high cost makes it unsuitable for rapid and routine clinical use, while microarrays exhibit poor sequence selectivity for miRNAs and are only semi-quantitative. Quantitative polymerase chain reaction (qPCR) assays are also challenging to develop for these very short RNAs (typically 18-24 nucleotides), and multiple enzymatic steps reduce sensitivity and limit multiplexing capacity.[7] Therefore improved ultrasensitive analytical platforms for short ribonucleic acids such as miRNAs are needed by the life sciences and clinical diagnostics communities[9-13].

In a particular embodiment illustrated herein we demonstrate a new method and systems to absolutely quantify miRNAs by high throughput single molecule counting in a flow cytometer.

SUMMARY OF THE INVENTION

One embodiment of the invention provides a method for quantifying microRNA at the single-molecule level in a biological sample, another embodiment provides a system, i.e., an ultrasensitive assay platform, for detection of nucleic acids, and particularly small nucleic acids like microRNAs (miRNAs, miRs, or micro ribonucleic acids). For example, in one embodiment, the method of the invention comprises:

1) extending the nucleic acid as a single-stranded DNA through rolling circle amplification and fluorescently labeling the extended microRNA by hybridization with fluorescent dyes conjugated to a single-stranded DNA, and in many embodiments incorporating an additional, select, fluorescent dye, e.g., by intercalation into the hybridized microRNA-single stranded DNA duplex, 2) exciting the fluorescently labeled extended nucleic acid and measuring the fluorescence emission from individual molecules of the fluorescently labeled extended microRNA, and 3) recording and analyzing the fluorescence emission detected.

In general terms, the present invention provides a method to count nucleic acids at the single-molecule level using flow cytometry after DNA extension and dense labeling with sequence-specific fluorophore conjugated dye-DNA hybridization probes, and a system designed to facilitate the methods. The platform of the invention, i.e., the method and system components that efficiently work with the method, allows high throughput and simultaneous detection of miRNAs across four orders of magnitude of concentration down to the single-molecule using accessible technology and materials available at non-prohibitive costs. The products can be spectrally barcoded to multiplex numerous sequences.

BRIEF DESCRIPTION OF THE DRAWINGS

FIG. 4A is a flow cytometry scatter plot showing events of microRNA amplicons labeled with both dye-DNA probes and SYBR® Green showing correlation between side scattering and SYBR® Green fluorescence intensity.

FIG. 4B shows data from the Cy5 and Cy3 channels for each event from the same flow cytometry experiment in FIG. 4A.

FIG. 5B-I shows flow cytometry gating of fluorescently labeled microRNA amplicons and elimination of spurious off-target events.

FIG. 7A-C show evaluation of microRNA amplificons through ensemble fluorescence intensity: 7A represents SYBR® Gold fluorescence intensity of rolling circle amplifications reactions with the indicated microRNA concentration; 7B shows dependence of SYBR® Gold fluorescence slope as a function of time on microRNA concentration during amplification reactions in (a), and 7C shows counts of microRNA products as a function of flow cytometry acquisition time, counts are zero for a product of a reaction containing no microRNA.

DETAILED DESCRIPTION OF THE INVENTION

Figure 1:
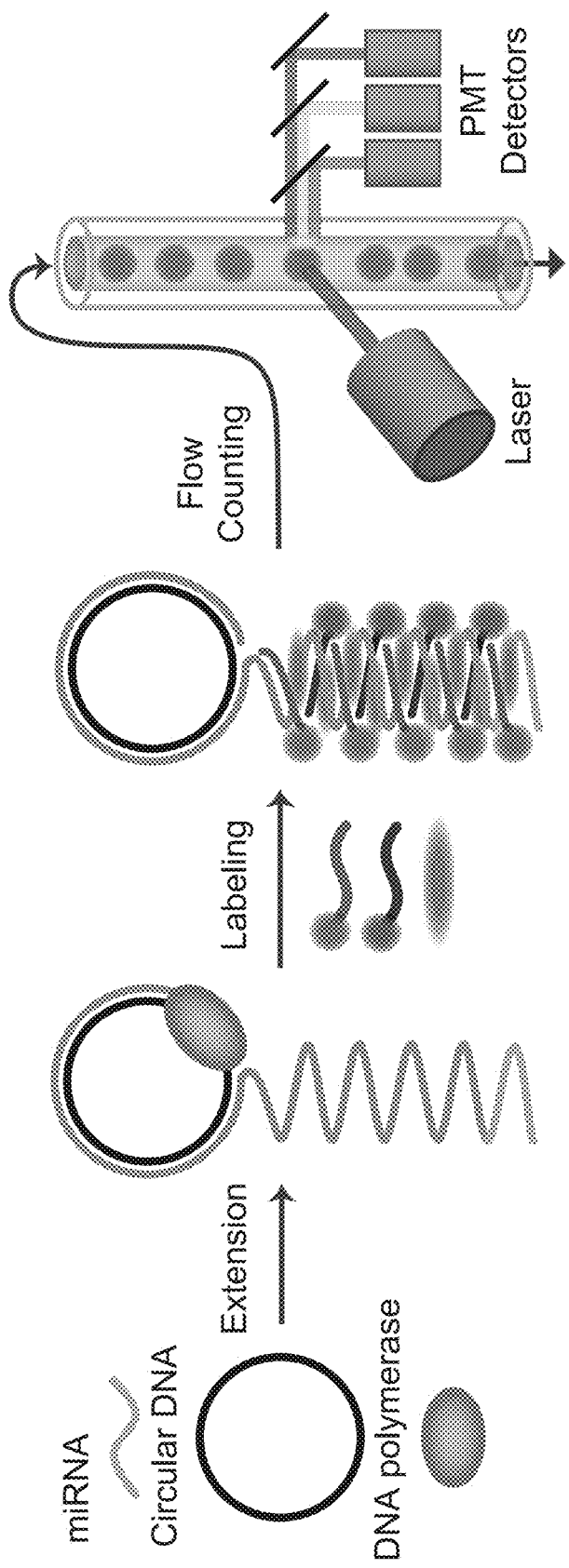
FIG. 1 is a schematic representation of the extension of single nucleic acid molecules by rolling circle amplification using a circular DNA template, followed by labeling with a mixture of multicolor dyes, e.g., SYBR® Green and dye-DNA probes, and detection based on multispectral fluorescence and scattering in a flow cytometer.

One embodiment of the invention provides a system for quantifying nucleic acids, in particular microRNAs, at the single-molecule level in a biological sample, the system comprising:
(1) a sub-system for extending the nucleic acid to form an amplicon, e.g., extending a nucleic acid as a single-stranded DNA amplicon through rolling circle amplification or other enzymatic reactions to form an amplicon
(2) a subsystem for labeling the amplicon with more than one fluorescent dye to form a labeled nucleic acid amplicon, wherein the labeled nucleic acid amplicon is labeled by:
   (i) hybridization of the nucleic acid amplicon with a fluorescent dye conjugated to a single-stranded nucleic acid or nucleic acid analog,
   (ii) binding or intercalation of single-stranded nucleic acid-specific or double-stranded nucleic acid-specific fluorescent dyes with the amplicon, and/or
   (iii) addition of the fluorescent dye into the nucleic acid amplicon by enzymatic incorporation of a fluorescent dye labeled nucleoside triphosphate or deoxyribonucleoside 5'-triphosphate,
(3) a fluorescence detection sub-system comprising excitation sources and corresponding fluorescence detectors for excitation of the fluorescently labeled amplicons and measurement of the fluorescence emission from individual molecules of the fluorescently labeled amplicon, and
(4) software to record and analyze the fluorescence emission from the detection subsystem.

In many embodiments, the singled-stranded amplicon is labeled by:
   (i) hybridization of the single-stranded DNA amplicon with a fluorescent dye conjugated to a single-stranded nucleic acid such as DNA or RNA, or nucleic acid analogs such as locked nucleic acids (LNAs) and peptide nucleic acids (PNAs),
   (ii) binding or intercalation of a, e.g., one or more, single-stranded or double-stranded DNA specific fluorescent dyes with the DNA amplicon, and/or
   (iii) incorporation of a, e.g., one or more, fluorescent dye into the single stranded DNA amplicon by enzymatic incorporation of a fluorescent dye labeled nucleoside triphosphate or deoxyribonucleoside 5'-triphosphate.

In many embodiments the measurement of the fluorescence emission is taken with a flow cytometer, and in many embodiments, the flow cytometer comprises the software to record and analyze the fluorescence emission.

In the present disclosure, unless indicated otherwise, "a" or "an" means one or more than one.

Typically, the singled-stranded DNA amplicon is labeled by more than one fluorescent dye. In some embodiments, the extended nucleic acid is fluorescently labeled by hybridizing said extended nucleic acid with a fluorescent dye conjugated to a single-stranded DNA, and intercalating said extended nucleic acid with additional fluorescent dyes.

Another aspect of the invention is a method for quantifying nucleic acid at a single molecule level in a biological sample, comprising:
(1) extending the nucleic acid to form an amplicon, for example, extending a nucleid acid as a single-stranded DNA amplicon through rolling circle amplification, and labeling the single-stranded DNA amplicon with more than one fluorescent dyes to form a labeled amplicon,
(2) exciting the fluorescently labeled amplicon, measuring the fluorescence emission from individual molecules of the fluorescently labeled amplicon,
(3) recording and analyzing data of the measured fluorescence emissions.

Useful excitation sources for the invention include, for example, a laser source, an incandescent light source, or a light emitting diode light source.

Many embodiments also comprise the step of minimizing or eliminating aberrant counts from the fluorescence emission from the individual fluorescently labeled single-stranded DNA amplicon and/or spectrally barcoding the fluorescently labeled single-stranded DNA amplicon to multiplex numerous sequences. As mentioned above, this can be accomplished using the software that makes up component 4 of the inventive system, which, in many embodiments, is conveniently part of a flow cytometer. In many instances, barcoding makes use of template sequences which results in a complementary amplicon sequence that can be fluorescently labeled in a sequence specific manner. These and other aspects of the present invention will become apparent from the disclosure herein.

The system and method of the invention are versatile and can be used for a variety of substrates and targets. For example, in some examples, the amplicon prepared in an initial step may comprise double-stranded DNA, single-stranded DNA, single-stranded RNA or a concatemer of RNA and DNA. The fluorescent dye-conjugated single-stranded nucleic acid may comprise primarily single-stranded DNA, single-stranded RNA, single-stranded peptide nucleic acid (PNA) or single-stranded locked nucleic acid (LNA). The fluorescent dye of the fluorescent dye-conjugated single-stranded nucleic acid may be one or more light emitting coumarin, cyanine, fluorescein, rhodamine, oxazine, Alexa, ATTO, or BODIPY, fluorescent phycobiliprotein, green fluorescent protein, DsRed dye, light-emitting semiconductor nanocrystal, or light-emitting organic polymer, nanoparticle, or bead. The target nucleic acid for quantitation may be double-stranded DNA, single-stranded DNA, microRNA (miRNA), messenger RNA (mRNA), long non-coding RNA (lncRNA), ribosomal RNA (rRNA), transfer RNA (tRNA), small nuclear RNA (snRNA), small nucleolar RNA (snoRNA), Piwi-interacting RNA (piRNA), interfering RNA (siRNA), antisense RNA (aRNA), transfer messenger RNA (tmRNA), tRNA-derived small RNA (tsRNA), rDNA-derived small RNA (srRNA), ribozyme, viral RNA or double-stranded RNA.

Counting Single Nucleic Acids

Figure 2A:
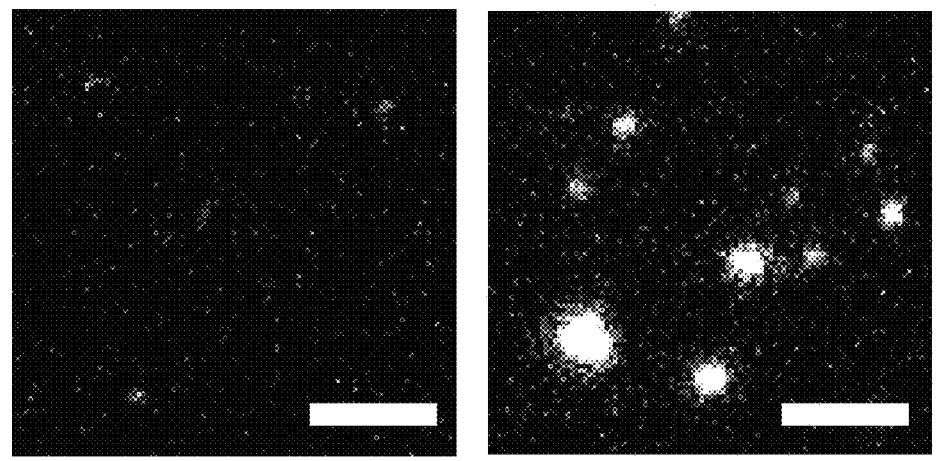
FIG. 2A shows single molecule images of Cy3-DNA probes (left) and Cy3-labeled microRNA amplicons (right) (scale bars=5 microns).
Figure 2B:
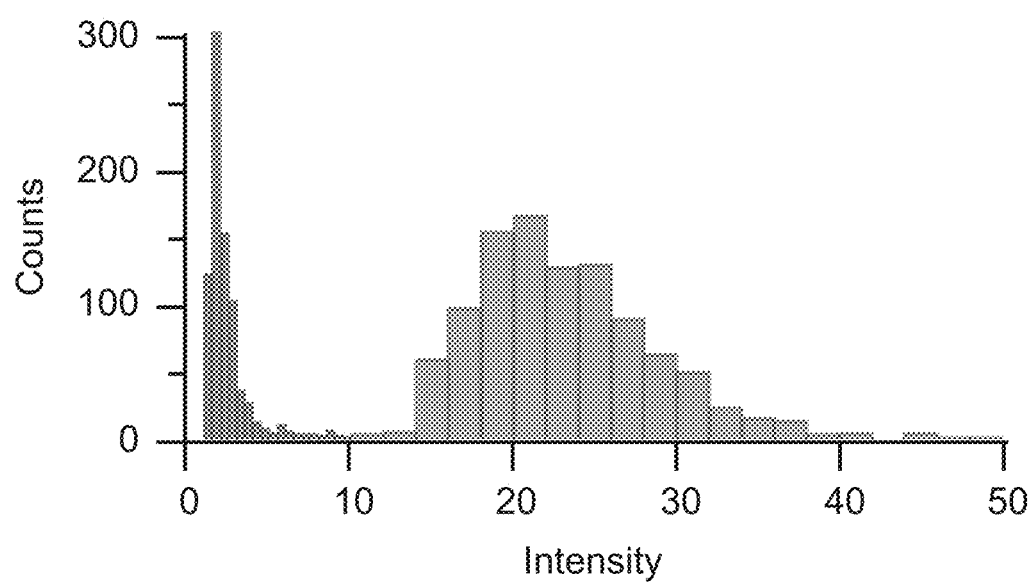
FIG. 2B shows intensity histograms (fluorescence micrographs) of Cy3-DNA probes (peaks on the left) and labeled microRNA amplicons (peaks on the right).
Figure 3:
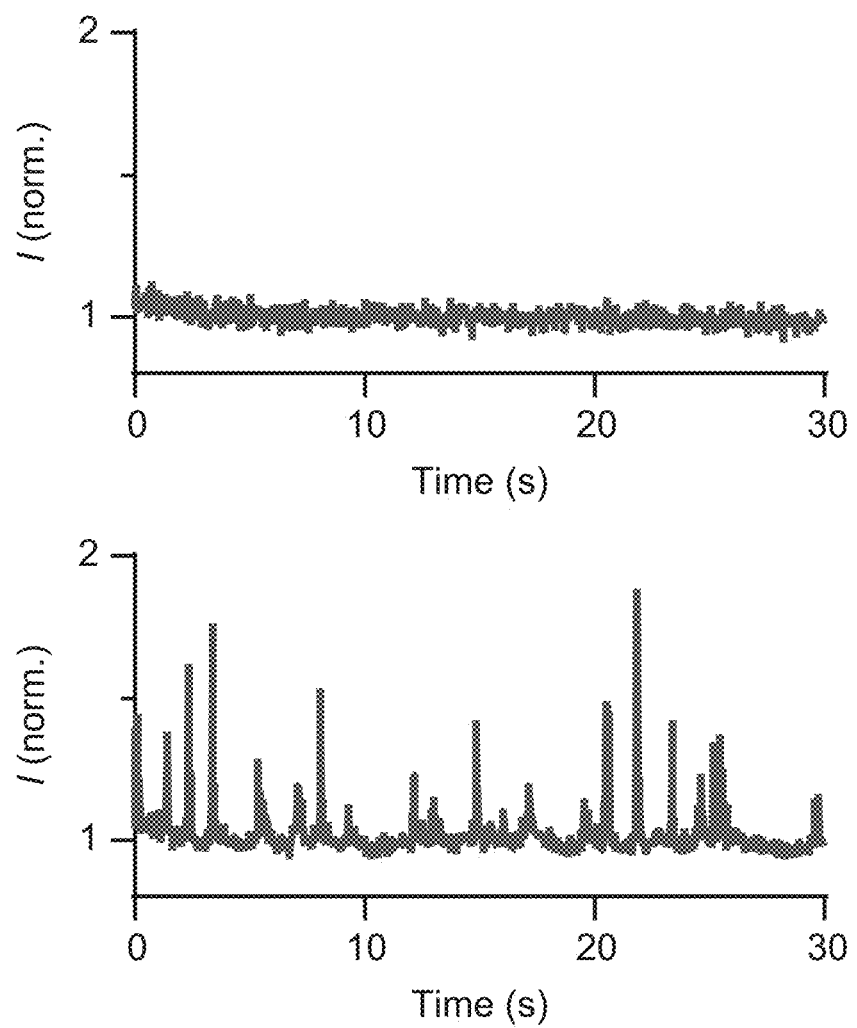
FIG. 3 shows temporal fluorescence intensity in a diffraction limited confocal spot for solution of free Alexa Fluor 430-DNA probes (top) and labeled microRNA amplicons (bottom).

The invention provides a new method called 'SM-Flow' to absolutely quantify nucleic acids by single molecule counting in a flow cytometer. The simple three-step process, i.e. extension, labeling, flow counting, is depicted schematically in FIG. 1: (1) the miR is extended from its 3' end as single-stranded DNA (ssDNA) through an enzymatic reaction such as rolling circle amplification (RCA), (2) the amplicon is then fluorescently labeled, e.g., through hybridization with dye conjugates of short Nucleic acids such as ssDNAs, direct incorporation of fluorescently labeled nucleotides into the extended DNA, or incorporation of a chemical dye such as an intercalating dye, e.g., a cyanine dye such as SYBR® Green that is capable of up to a 1000× fluorescence enhancement upon binding to dsDNA[14-15], and (3) finally the labelled amplicons are rapidly counted using a flow cytometer. For example, miR-375, which is an exosomal blood biomarker that is a prognostic indicator for survival in castration resistant prostate cancer[16,17,] has been successfully employed. Through RCA amplification, miRs grow to molecules that are e.g., 1,000 times larger than their original size (average>25 kbp) and after fluorescent labeling are immensely bright, allowing detection as distinct puncta amid a large excess of dim probes. When imaged as spots on a coverslip through fluorescence microscopy, the labeled products are 11 times brighter than individual dye-ssDNA probes (FIG. 2) and can be larger than the ~200 nm optical diffraction limit. Confocal imaging of a diffraction-limited spot in the reaction solution reveals fluorescent molecules with intensities much brighter than the dye probe background signals (FIG. 3) with diffusion coefficients orders of magnitude smaller than those of the dye probes.

The labeled RCA products are bright enough to easily register as events in a conventional benchtop flow cytometer with photomultiplier tube detectors, normally used to measure large scattering particles with dimensions spanning hundreds of nanometers to tens of microns, such as blood cells and microbes. To ensure that counts correspond with nucleic acid products rather than noise, signals from multiple fluorescent labels are correlated with optical scattering events using multiparametric gating, to eliminate aberrant counts that are substantial when using individual parameters alone.

Unlike qPCR and other methods for nucleic acid detection, commercial grade flow cytometers allow both counting and multispectral optical analysis of individual molecules. This unique capability allows nucleic acids such as miR amplicons to be characterized using multiple fluorescent labels and optical scattering events so that multiparametric gating can be used to differentiate true amplicon signals from aberrant signals that can contribute approximately half of the events in individual parameter channels. FIG. 4A shows a first level of gating based on side scatter signal and the fluorescence intensity of the intercalating dye SYBR® Green. SYBR® Green exhibits a 1000-fold fluorescence enhancement upon binding to dsDNA. Data show a band of events with nearly linear proportionality ($R^2$=0.953), a relationship resulting from the proportionality between side scattering intensity, dielectric particle size,[18] and the linearity of SYBR® Green fluorescence with dsDNA quantity.[19] FIG. 4B shows that the majority of detected events also correspond to molecules proportionally bound by sequence specific dye-DNA probes labeled with cyanine dyes Cy5 and Cy3. By sequentially applying multiparametric gates from the distinct optical channels, 99.95% of the false positive events are eliminated while 87.76% of events corresponding to amplicon signals present in all gates are maintained, see FIG. 5B-I.

FIGS. 5B-I shows flow cytometry gating of miR amplicons fluorescently labeled with intercalating dye SYBR® Green and dye-DNA hybridization probes and elimination of spurious off-target events. FIG. 5B shows a scatter plot of side scattering and SYBR® intensity for labeled amplicons from 1 nM miR-375 solutions. The polygon outlined in dark lines indicate gate regions to designate events corresponding to miR amplicons. FIG. 5C shows events and gating from 5B with aberrant events eliminated based on Cy3-Cy5 gating (see 5F). Few events are outside of the scatter-SYBR® gate. FIG. 5D is a scatter plot of side scattering and SYBR® intensity for labeled amplicons from 0 nM miR-375 control solutions. The dark lines indicate the same polygonal gate region generated in FIG. 5B. FIG. 5E shows events and gate from FIG. 5D with points eliminated based on Cy3-Cy5 gating (see 5H). Very few events are detected in this negative control. FIG. 5F is a scatter plot of Cy3 and Cy5 intensity for labeled amplicons from 1 nM miR-375 solutions. The gate region is indicated by the dark lined polygon to designate events corresponding to miR amplicons. FIG. 5G shows events and gate from 5F with events eliminated based on side scatter and SYBR® gating (see FIG. 5B). Few events are outside of the Cy3-Cy5 gate. FIG. 5H is a scatter plot of Cy3 and Cy5 intensity for labeled amplicons from 0 nM miR-375 control solutions. The dark lined polygon indicates the same gate region generated in panel FIG. 5F. FIG. 5I shows events and gate from FIG. 5H with points eliminated based on side scatter and SYBR® gating (see FIG. 45D). Very few events are detected in this negative control.

Figure 6A:
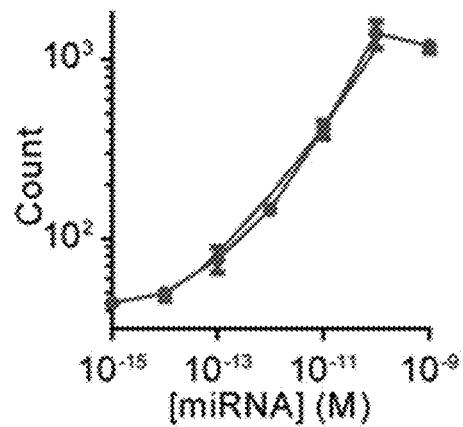
FIG. 6A shows correlation between event counts and microRNA concentration, as circles with standard deviation error bars. Unmarked line shows the linear dynamic range.
Figure 6B:
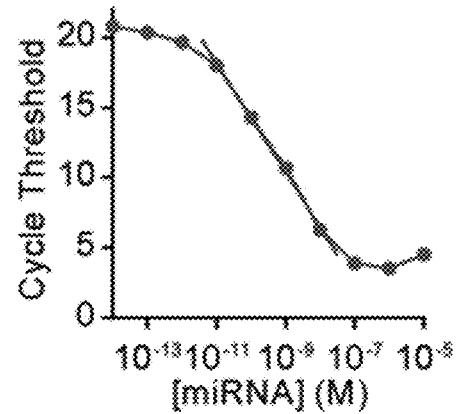
FIG. 6B shows correlation between cycle threshold and microRNA concentration using qPCR as circles with standard deviation error bars. Unmarked line shows the linear dynamic range.
Figure 6C:
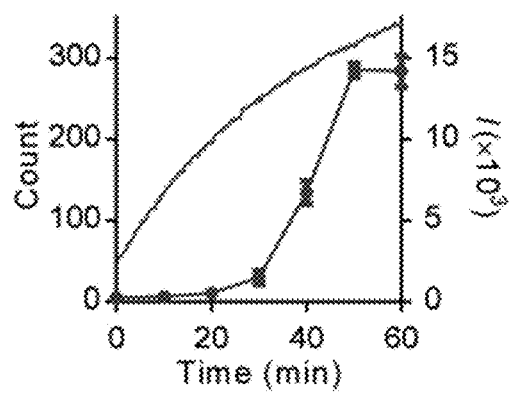
FIG. 6C shows microRNA counts after different RCA reaction times, shown as circles with standard deviation error bars, compared with ensemble fluorescence intensity from SYBR® Gold, unmarked line.

The measured counts are stoichiometrically proportional to the number of miR targets present. FIG. 6A shows the number of counts measured over 15 seconds from solutions containing seven different concentrations of miR-375, with all other conditions held constant, including the concentration of all of the fluorescent probe labels. Single-molecule counting of miR-375 give a detection limit of 47.0 fM and a dynamic range spanning more than four orders of magnitude, with an upper limit of detection of 100 pM. This wide range is important when working with miRs due to the wide range of concentrations of distinct sequences in biological fluids and cells.[20] The specificity for miR-375 is sufficient to quantitatively measure the analyte over a similar range in RNA extract from human plasma. In comparison, conventional analysis of RCA products based on net SYBR® Gold intensity using a qPCR instrument give a limit of detection of 36.5 pM, nearly a thousand times higher than that for counting using the flow cytometer. Gold-standard q-PCR using a commercial kit gave a 3.7 pM detection limit, FIG. 6B, nearly 100 times higher. Notably, over the course of the isothermal RCA extension reaction, the SM-Flow count rises abruptly and plateaus while the RCA ensemble fluorescence intensity deriving from SYBR® enhancement continuously rises, FIG. 6C, indicating a specific size threshold for detection using a flow cytometer. During flow counting, the count number increases linearly with time, suggesting that sensitivity can be boosted simply by acquiring data for longer durations, FIG. 7A-C.

Compared with conventional surface-based single molecule measurements, where nonspecific adsorption is a dominating factor in analytical sensitivity, this solution-based single molecule counting procedure does not require laborious surface functionalization that can be difficult to reproducibly control. Unlike qPCR and other ensemble fluorescence methods for nucleic acid detection, the method of the invention allows both counting and analysis of individual molecules, so spectral barcoding can be used to multiplex the detection of multiple miR sequences in mixtures.

Figure 8:
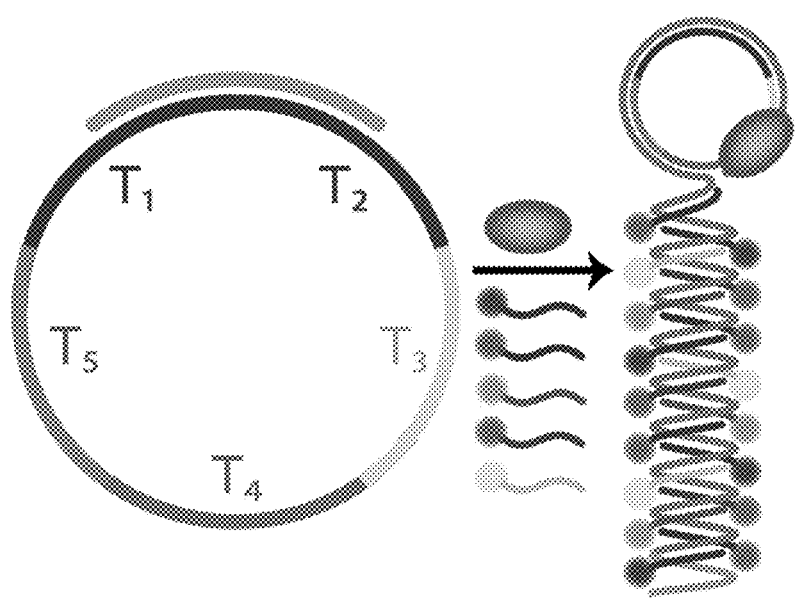
FIG. 8 shows a schematic depiction of multicolor labeling of an RCA amplicon based on sequence-specific dye-DNA hybridization to five template-dependent target sequences, T1 to T5.

That is, in addition to increasing amplicon recognition specificity, in many embodiments multiparametric single-molecule analysis is used to spectrally barcode miRs for independent quantification based on distinguishable fluorescence profiles. As multispectral fluorescence detection is a standard capability of commercial grade benchtop flow cytometers, circular RCA templates with 5 variable dye-DNA probe binding sites were designed, which can be modified to generate amplicons with unique fluorescent fingerprints when hybridized to complementary probes, FIG. 8.

Fluorescence spectral signatures were measured as intensity ratios between different fluorescent bands. The multiplexing capacity (M) for this type of spectral encoding increases with the number of fluorophore bands (k) and ratiometric intensity levels (n) as[21]

$$M = \frac{(n+k-1)!}{k!(n-1)!}$$

As M grows exponentially with both k and n high degrees of multiplexing can potentially be achieved.

Figure 9:
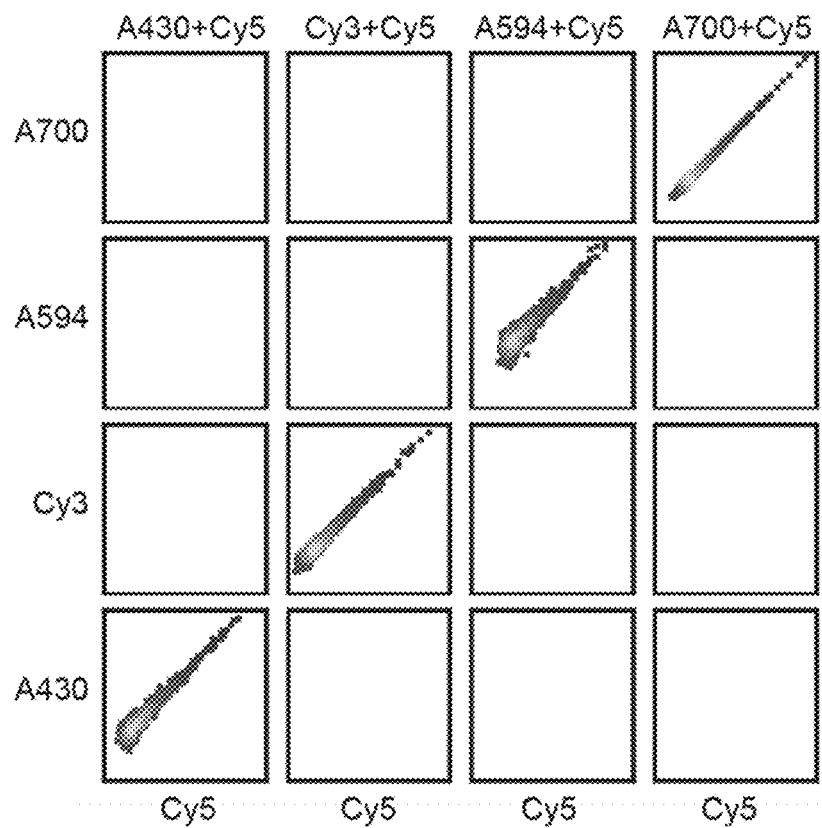
FIG. 9 shows event count density plots in biparametric color channels using dye combinations indicated along the top. Axes are logarithmically scaled
Figure 10A:
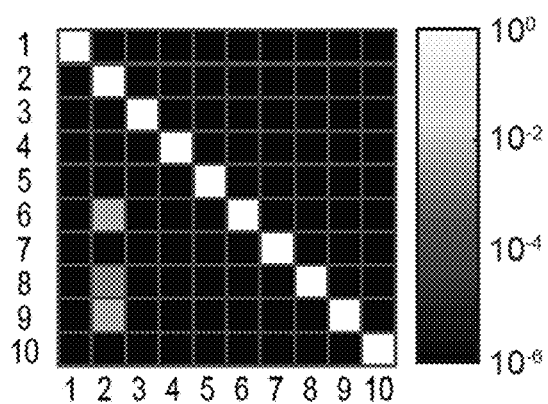
FIG. 10A shows a heat map representing false positive count rates for biparametric color channels corresponding to numerical labels in Table 1. Fluorophore pairs are plotted on the y axis, optical channels are plotted on the x axis.

To characterize the capacity for differentiating amplicons using colorimetric gating, miR amplicons were labeled with pairs of 5 distinct fluorophores through dye-DNA hybridization. See Table 1. FIG. 9 shows example data in biparametric channels after side scatter-SYBR® gating and color channel compensation. Of the 90 channels analyzed, 87 exhibited no detectable off-target events compared with more than 10,000 events in on-target channels, FIG. 10A.

TABLE 1

| Fluorophore pairs | |
|---|---|
| Code | Fluorophore Pair |
| 1 | Alexa Fluor 430/Alexa Fluor 594 |
| 2 | Alexa Fluor 430/Cy3 |
| 3 | Alexa Fluor 430/Cy5 |
| 4 | Cy5/Alexa Fluor 700 |
| 5 | Alexa Fluor 430/Alexa Fluor 700 |
| 6 | Alexa Fluor 594/Alexa Fluor 700 |
| 7 | Alexa Fluor 594/Cy5 |
| 8 | Cy3/Alexa Fluor 594 |
| 9 | Cy3/Alexa Fluor 700 |
| 10 | Cy3/Cy5 |

Figure 10B:
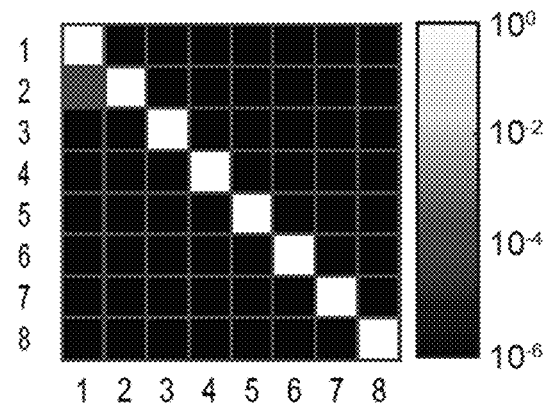
FIG. 10B Heat map of empirical false positive count rates between ratiometric channels corresponding to numerical labels provided in Table 2, fluorophore pairs are plotted on the y axis, optical channels are plotted on the x axis.
Figure 11A:
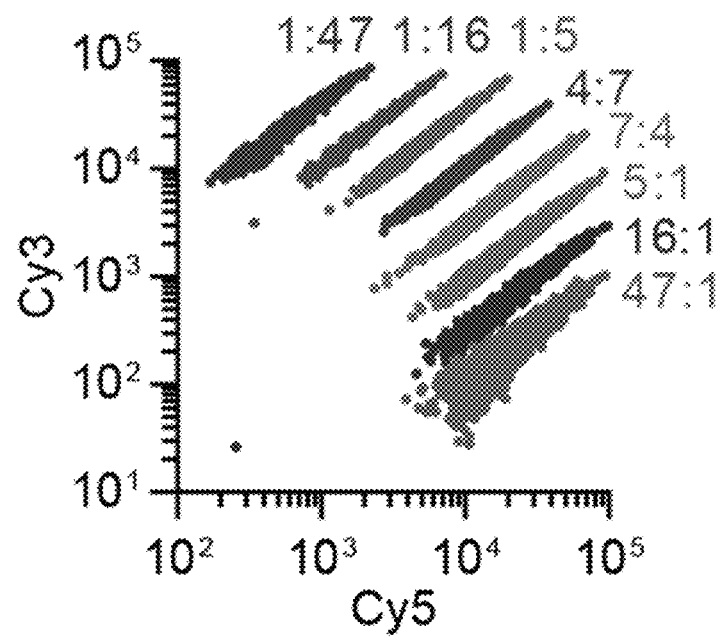
FIG. 11A Ratiometric labeling of microRNA amplicons showing discrete bands with narrow intensity profiles, 10 pM microRNA concentrations and >79,000 counts.

The capacity to further encode amplicons by ratiometric fluorescence intensity within a single biparametric channel was then characterized by precisely tuning the relative abundance of bound dye-DNA probes. FIGS. 10B and 11A show that ratiometric labeling results in narrow bands within a single biparametric intensity space. The 8 ratios of Table 2 are shown in FIGS. 10B and 11A and exhibit very little overlap reflecting the large size and dense labeling of the products.

TABLE 2

| Code | Ratio (Cy3:Cy5) |
|---|---|
| 1 | 47:1 |
| 2 | 16:1 |
| 3 | 5:1 |
| 4 | 7:4 |
| 5 | 4:7 |
| 6 | 1:5 |
| 7 | 1:16 |
| 8 | 1:47 |

Figure 11B:
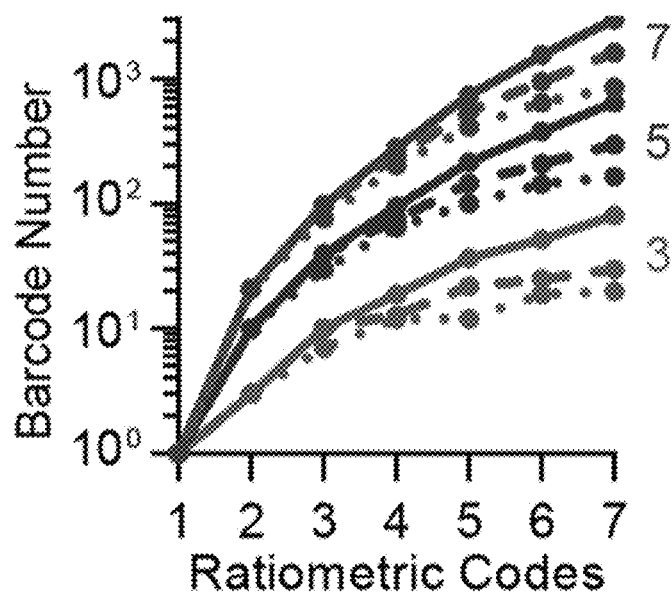
FIG. 11B illustrates calculated optical barcode numbers for indicated color code number and ratiometric code number. 7 blue combinations, top three lines, 5 red combinations, three middle lines, and 3 green color combinations, bottom three lines. Solid curves represent total code numbers, dashed and dotted lines indicate code numbers with maximum false positive count rates of $10^{-3}$ and $10^{-6}$, respectively.
Figure 12:
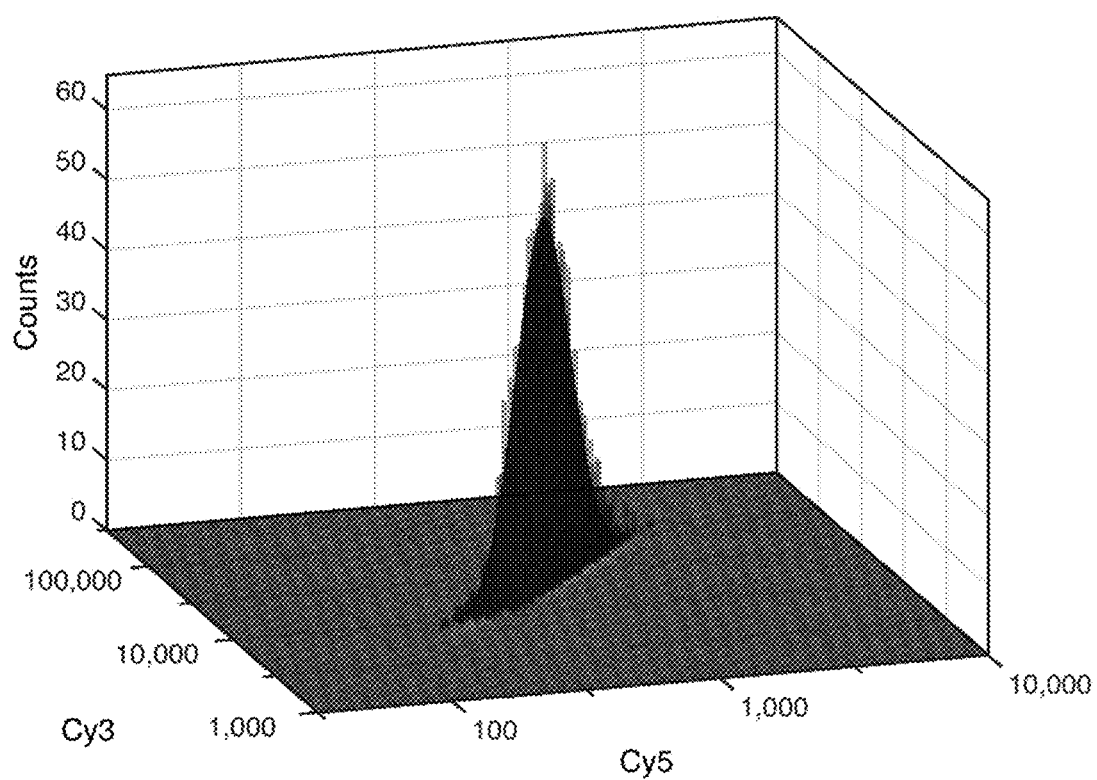
FIG. 12. Bar graph showing binned events in the Cy3 and Cy5 color channels overlayed on a two-dimensional elliptical Gaussian function.

These ratiometric amplicon data fit well to elliptical Gaussian functions ($R^2 > 0.95$; FIG. 12) enabling the calculation of absolute sensitivity and specificity for ratiometric amplicon differentiation. For the Cy5:Cy3 pair analyzed with a ratio range between 1:47 and 47:1, as many as 16 distinguishable codes could be generated with fewer than one in one million false positive counts in any single channel. The maximum number of optical barcodes for this labeling scheme is shown in FIG. 11B, showing the independent effects of fluorescence color number and ratiometric code number, in addition to the effects of signal crosstalk between channels that result in false positive rates of either $10^{-3}$ (dotted lines) or $10^{-6}$ (dashed lines).

Circular RCA templates can be easily generated with 6 unique probe binding sites so that the RCA products can be barcoded with 6 distinct fluorescent ssDNA-dye conjugates.[22-24] However, there is an intrinsic tradeoff between multiplexing capacity and detection limit, as occasional counts in an adjacent channel will yield false positives. This is extremely important for miRs due to their wide concentration that span orders of magnitudes for distinct sequences in biological fluids and cells.

This work describes the first use of benchtop flow cytometers to count small nucleic acids. Flow cytometers have been widely used for high throughput analysis of individual cells, isolated nuclei, chromosomes, virions, biogenic extracellular vesicles[25] nanoparticles, and objects with dimensions that are thousands to millions times greater than miRs.

We show that RCA as used in the present invention allows for the growth of tiny miRs into giant products that are detectable after labeling as discrete events by scattering or fluorescence intensity in a flow cytometer. Commercially available reagents are used to maintain molecular stoichiometry for accurate molecular counting. The method of the invention can be widely adopted due to the extensive availability of flow cytometers across clinical and research laboratories.

With a wide range of methods now available to isothermally grow and label nucleic acids in complex solutions,[26-29] extension of the present methods to a wide array of mRNA and DNA targets, and the use of flow sorting to isolate and characterize specific target nucleic acid populations is simple. A large number of optical barcodes also provides the potential to multiplex the detection of miRs, with a capacity approaching the number of endogenous human miRs (4076).[29] As a result of its high sensitivity, high throughput, simplicity, multiplexing, and wide availability of flow cytometry instrumentation, the present invention has the potential for wide-scale adoption in research as well as clinical applications for which nucleic acids such as miRs serve as diagnostic and prognostic biomarkers.

Specific aspects of the invention are illustrated below.

Chemicals and Reagents

No. 1.5 coverglass was purchased either as 50-well chambers from Electron Microscopy Sciences). Monomethoxy monosuccinimidyl ester poly(ethylene glycol) (mPEG5000-NHS, 5000 Da), and monoazido monosuccinimidyl ester poly(ethylene glycol) (azide-PEG5000-NHS, 5000 Da) were purchased from Nanocs, Inc. Sodium hydroxide (>97%), glacial acetic acid (>99.7%), and sodium bicarbonate (>99.7%) tris(hydroxymethyl)-aminomethane (Tris Base), Tween 20, ethylenediaminetetraacetic acid (EDTA), SYBR® Green I Nucleic Acid Gel Stain (SYBR® Green), and SYBR® Gold Nucleic Acid Gel Stain (SYBR® Gold) were also purchased from ThermoFisher Scientific. Deoxynucleotide Solution Mix (dNTP), phi29 DNA polymerase (φ29 polymerase), and E. coli Exonuclease I were purchased from New England Biolabs. 10% Mini-PROTEAN® TBE-Urea Gel (4566033), 2×TBE-Urea sample buffer, and 10×TBE Urea were purchased from Bio-Rad laboratories. CircLigase II was purchased from Lucigen. DNA or RNA oligonucleotides (oligos) with sequences shown in Table 3 were purchased from Integrated DNA Technologies. Phosphate-buffered saline (PBS) was purchased from Corning. In-house purified Milli-Q water was used throughout. Unless specified, all other chemicals and solvents were purchased from Sigma-Aldrich and used without further purification.
21-28

TABLE 3

Oligonucleotide sequences

| Name | Sequence | SEQ ID NO: |
|---|---|---|
| miR375 | rUrUrUrGrUrUrCrGrUrUrCrGrGrCrUrCrGrCrGrUrGrA | 1 |
| RCA Template | /5Phos/CAACAACCAACAAACACAGAATGCTCACGCGAGCCGAACGAAC AAACCTCAGCAACACCAAACAACAAAC | 2 |
| A405-DNA | /5Alex405N/CCT CAG CAA CAC C | 3 |
| Amplicon Capture DNA | /5DBCOTEG/ACT TTA CTT TAC TTT ACT TTA CTT TAC TTT ACT TTA CTT TAC TTT ACT TTA CTT TAC TTT ACT TTA CTC ACG CGA GCC GAA CGA ACA AA | 4 |
| A430-DNA | /5Alex430N/CCT CAG CAA CAC C | 5 |
| Cy3-DNA | /5Cy3/CCT CAG CAA CAC C | 6 |
| A594-DNA | /5Alex594N/CCTCAGCAACACC | 7 |
| Cy5-DNA | /5Cy5/CCT CAG CAA CAC C | 8 |
| Cy5-DNA T2 | /5Cy5/ACA CAG AAT GCT | 9 |
| A700-DNA | /5Alex700N/CCT CAG CAA CAC C | 10 |

/5Phos/ indicates 5' phosphate group modification.
/5DBCOTEG/ indicates 5'-dibenzocyclooctyne (DBCO) modification.
/5Alex430N/, /5Cy3/, /5Alex594N/, /5Cy5/, and /5Alex700N/ indicate 5' modifications with the dyes Alexa Fluor 430, Cy3, Alexa Fluor 594, Cy5, and Alexa Fluor 700, respectively.

Circular Template Preparation

Circularization of the 5'-phosphoryl RCA Template (Table 3) was performed at 2 μM using CircLigase II (2.5 U/μL) in CircLigase Buffer (0.33 M Tris-acetate, 0.66M potassium acetate, 2.5 mM MnCl$_2$, and 5 mM dithiothreitol at pH 7.5) for 1 hr at 60° C.[29] Unreacted linear DNA was removed by reaction with exonuclease I for 1 hr at 37° C. followed by a 10 min incubation at 80° C.

Rolling circle miRNA labeling. Circular RCA Templates (100 nM) were hybridized with miR375 (10 nM) in polymerase buffer (50 mM Tris-HCl, 10 mM MgCl$_2$, 10 mM (NH$_4$)$_2$SO$_4$, and 4 mM dithiothreitol at pH 7.5) for 4 hr at room temperature. RCA was then initiated through the addition of a 2× reaction mixture (0.5 U/μL φ29 DNA Polymerase, 200 nM dNTPs, 0.2 mg/mL BSA, and 0.01% SYBR®Gold). Reactions were performed using an Eppendorf Realplex 4S Real-time PCR system with SYBR® Gold fluorescence monitored using LED excitation at 470 nm and emission at 520±10 nm at 30 s intervals. Reactions were allowed to proceed for 1 hr at 37° C. prior to polymerase heat inactivation at 95° C. for 5 min. For time course studies, reaction mixtures were stored on ice until reaction initiation at 37° C., and all reactions were heat inactivated in tandem at 95° C. for 5 min. Samples were then stored at −20° C. prior to subsequent analysis.

microRNA amplicon labeling. RCA reaction solutions were diluted 20× in a solution containing dye-DNA probes at a final concentration of 3 nM in a phosphate buffer (10 mM $Na_2HPO_4$, 1.8 mM $KH_2PO_4$, 2% BSA, pH 7.4) containing SYBR® Green at a final concentration of 0.0316%. Samples were mixed thoroughly and denatured by incubation at 50° C. for 10 min, followed by 4 hr of annealing at room temperature.

Flow-based single-molecule data collection. Labeled microRNA amplicons were transferred to round-bottom polystyrene tubes for loading into the flow cytometer. All acquisition parameters were tested prior to each experiment using Flow-Check Fluorospheres to confirm that emission parameters were within expected intensity ranges. Samples were run with a flow rate of 35 µL $min^{-1}$. Events were recorded for intensities greater than 200 r.f.u for side scattering, SYBR®, and the dyes used for labeling by hybridization. Photomultiplier voltage of 450 V was used for all samples. Data were collected with a 15 s acquisition time and 8.75 µL $min^{-1}$ flow rate. Laser and filters used for each probe are provided in Table 4. Fluidics were cleaned with desalinated water to remove residual sample between experiments.

TABLE 4

Flow cytometer lasers and optical filters.

| Target | Laser Wavelength (nm) | Longpass Filter (nm) | Bandpass Filter (nm) |
| --- | --- | --- | --- |
| Alexa Fluor 430 | 403 | 505 | 525/30 |
| Side Scatter | 488 | N.A. | 488/10 |
| SYBR ® Green | 488 | 505 | 530/30 |
| Cy3 | 561 | N.A. | 582/15 |
| Alexa Fluor 594 | 561 | 595 | 610/20 |
| Cy5 | 640 | N.A. | 670/30 |
| Alexa Fluor 700 | 640 | 685 | 730/45 |

Data analysis. Flow cytometry data was analyzed using FCS express software. Amplicon signals were gated based on the intensity of side scattering and SYBR® Green fluorescence as an initial means of isolating signals corresponding to large particles and double stranded DNA, respectively. Gated signals were then further analyzed based on the intensity of probe fluorescence with Cy3 and Cy5 intensity used unless otherwise noted. When analyzing multiple fluorophore combinations, fluorescence intensity values were compensated to account for fluorescence overlap between fluorophores with overlapping excitation and emission spectrums. Compensation was performed using samples containing only one class of fluorophore probe to establish baseline controls for automated compensation. Automated gates were then further optimized to maximize the discrimination of different populations.

DNA stock resuspension, quantification, and storage. DNA oligonucleotides were all purchased from Integrated DNA Technologies (Coralville, Iowa). Stocks were resuspended in nuclease free water following a 5 min centrifugation at 5000 g. DNA was analyzed with a Nanodrop 1000 (Thermo Scientific, Waltham, Mass.) with concentration quantified based on absorbance at 260 nm and purity characterized based on A260/A280 ratio. All stocks were stored at −20° C. prior to use.

Characterization of nonspecific signal between intensity gated populations. Each in a series of dye-DNA probes were initially prepared with each possible 2-fluorophore combinations using the hybridization conditions optimized as above. Each dye mixture was then used to dilute 2.5 µL of a 1 nM RCA reaction 50× to a final volume of 200 µL. Automatic compensation was then performed using samples containing only 1 dye to account for fluorescence overlap between different dyes, and manual optimization was performed to minimize signal overlap. Side scattering and SYBR® Green gates were then applied to isolate amplicon signals from background fluorescence. Finally, independent gates were generated for each of the 2-fluorophore combinations. Particle counts corresponding to the number of particles present in each of the gates were then recorded for each of the 2-fluorophore combinations, and data was normalized based on the total number of particles counted in each gate. All particle counts not corresponding to a 2-fluorophore gate other than their own were then counted as non-specifically detected particles. Constants corresponding to the average number of non-specific spots present for a given gate were then reported. Intensity gate mean false positive rate $\overline{FP}$ corresponding to the average number of non-specific counts present for a given gate were then reported with error bars indicating the standard deviation of background counts between independent populations.

Characterization of nonspecific signal between fluorescence type gated populations. Cy3-DNA and Cy5-DNA probes were prepared at a variety of concentration ratios using the hybridization conditions optimized as above. Dye mixtures were used to dilute RCA reactions 50× to a final volume of 200 µL. Automatic compensation was then performed using samples containing 1 dye to account for fluorescence overlap between different dyes, and manual optimization was performed to minimize signal overlap. Side scattering and SYBR® Green gates were then applied to isolate amplicon signals from background fluorescence. Finally, independent gates were generated for each of the samples containing different ratios of Cy3-DNA and Cy5-DNA probes. Particle counts corresponding to the number of particles present in each of the gates were then recorded for each of the ratio value, and data was normalized based on the total number of particles in each gate. All particle counts not corresponding to a ratio gate other than their own were then counted as non-specifically detected particles. Fluorescence type gate mean false positive rate $\overline{FP}$ corresponding to the average number of non-specific counts present for a given gate were then reported with error bars indicating the standard deviation of background counts between independent populations.

RNA extraction from human plasma. RNA present in pooled healthy human plasma (Innovative Research) was extracted though the addition of 0.75 mL of TRIzol™ LS Reagent (Invitrogen) to 0.25 mL of plasma. Samples were then homogenized through pipetting and allowed to incubate for 5 min at room temperature. Chloroform (0.2 mL) was then added to each tube and allowed to incubate for 3 min. Samples were then centrifuged for 15 min at 12,000 g. RNA in the aqueous phase was transferred to a new tube and precipitated with the addition of 0.5 mL of isopropanol and allowed to incubate for 10 min before centrifugation at 12,000 g for 15 min at 4° C. The supernatant was then removed, and RNA was resuspended in 75% ethanol prior to centrifugation at 7500 g for 5 minutes at 4° C. The supernatant was then removed, and the RNA was allowed to air dry for 10 min before resuspension in RNAse-free water. Samples were stored at −20° C. until use.

Measuring optical barcode crosstalk between colors. Labeling of RCA amplicons (from 1 nM miR-375) was performed as described above with the following modifications. All binary combinations of 5 dye-DNA probes were used to dilute the amplicon solution (2.5 µL) 50-fold. Automatic compensation was performed using samples containing single dye-DNA, followed by manual optimization to minimize signal overlap. Side scattering and SYBR® Green gates were then applied to isolate amplicon signals and independent gates were generated for each of the 2-fluorophore combinations. Counts corresponding to the number of amplicons present in each of the gates were then recorded for each of the 2-fluorophore combinations, and data were normalized based on the total number of counts in each gate. All counts corresponding to a 2-fluorophore gate other channels corresponding to the used dyes were counted as false positives.

Measuring optical barcode crosstalk between ratios. Labeling of RCA amplicons (from 1 nM miR-375) was performed as described above with the following modifications. Mixtures of Cy3-DNA and Cy5-DNA dye-DNA probes at a fixed total concentration and varying Cy3-DNA: Cy5-DNA ratios were used to dilute RCA reactions 50-fold to a final volume of 200 µL. After color channel compensation, side scattering and SYBR® Green gates were then applied to isolate amplicon signals from background fluorescence. Finally, independent gates were generated for each of the samples containing different ratios of Cy3-DNA and Cy5-DNA probes and event counts were recorded. All counts corresponding to a probe intensity ratio gate other channels corresponding to the applied ratio were counted as false positives.

Estimating optical barcode numbers. A Matlab code was written to generate all possible barcodes for a given combination of fluorescent label numbers and hybridization probe binding sites on the circular DNA template. Codes were removed if they yielded equivalent multicolor intensity ratios due to the broad linear range of intensities observed for the miR amplicon bands. Crosstalk between different ratiometric intensities was estimated based on data in FIG. 11A for Cy3 and Cy5 labels, and crosstalk between color channels was assumed to be zero. Each plot was fit to a two-dimensional elliptical Gaussian function to calculate overlap integrals between pairs of ratiometric barcodes with equal enclosed volumes, with Gaussian function symmetry assumed to extend in all color dimensions. The overlap integrals for all pairwise ratios were then summed to calculate the total false positive rate for each code, and codes with the highest false positive count were then individually eliminated. This process was repeated iteratively until the maximum number of codes was generated for which all maximum false positive rates were either $10^{-3}$ or $10^{-6}$.

REFERENCES

1. Berezikov, E. Nat. Rev. Genet. 12, 846-860 (2011).
2. Gebert, L. F. R. & MacRae, I. J. Nat. Rev. Mol. Cell Biol. 20, 21-37 (2019).
3. Mitchell, P. S. et al. Proc. Natl. Acad. Sci. U.S.A. 105, 10513-10518 (2008).
4. He, Y. et al. Clin. Chem. 61, 1138-1155 (2015).
5. Keller, A. et al. Nat. Methods 8, 841-843 (2011).
6. Skog, J. et al. Nat. Cell Biol. 10, 1470-1476 (2008).
7. van Rooij, E. The Art of MicroRNA Research. Circ. Res. 108, 219-234 (2011).
8. Witwer, K. W. Clin. Chem. 61, 56-63 (2015).
8a. van Rooij, E. Circ. Res. 108, 219-234 (2011).
9. Hunt, E. A., Broyles, D., Head, T. & Deo, S. K. Ann. Rev. Anal. Chem. 8, 217-237 (2015).
10. Johnson-Buck, A. et al. Nat. Biotechnol. 33, 730-732 (2015).
11. Zhou, X. et al. Nat. Mater. 14, 1058-1064 (2015).
12. Huang, S., Romero-Ruiz, M., Castell, O.K., Bayley, H. & Wallace, M. I. Nat. Nanotech. 10, 986-991 (2015).
13. Tavallaie, R. et al. Nat. Nanotech. 13, 1066-1071 (2018).
14. Tuma, R. S. et al. Characterization of SYBR® Gold Nucleic Acid Gel Stain: A Dye Optimized for Use with 300-nm Ultraviolet Transilluminators. Anal. Biochem. 268, 278-288 (1999).
15. Dragan, A. I. et al. SYBR® Green I: Fluorescence properties and interaction with DNA. J. Fluoresc. 22, 1189-1199 (2012).
16. Huang, X. et al. Eur. Urol. 67, 33-41 (2015).
17. Wang, Y. et al. Mol. Cancer 15, 70 (2016).
18. Mage, P. L. et al. Nat. Mater. 18, 82-89 (2019).
19. Vitzthum, F., Geiger, G., Bisswanger, H., Brunner, H. & Bernhagen, J. Anal. Biochem. 276, 59-64 (1999).
20. Liang, Y., Ridzon, D., Wong, L. & Chen, C. J. B. G. BMC Genomics 8, 166 (2007).
21. Weisstein, E. W. Ball Picking. Available at: http://mathworld.wolfram.com/BallPicking.html. (Accessed: 24 Oct. 2018)
22. Shikha, S., Salafi, T., Cheng, J. & Zhang, Y. Versatile design and synthesis of nano-barcodes. Chem. Soc. Rev. 46, 7054-7093 (2017).
23. Ullal, A. V et al. Cancer cell profiling by barcoding allows multiplexed protein analysis in fine-needle aspirates. Sci. Tranl. Med. 6, 219ra9 (2014)
24. Krutzik, P. O., Clutter, M. R., Trejo, A. & Nolan, G. P. Fluorescent Cell Barcoding for Multiplex Flow Cytometry. in Current Protocols in Cytometry Chapter 6, Unit 6.31 (John Wiley & Sons, Inc., 2011).
25. van der Pol, E. et al. J. Thromb. Haemost. 12, 1182-1192 (2014).
26. Rouhanifard, S. H. et al. Nat. Biotechnol. 37, 84-89 (2018).
27. Choi, H. M. T., Beck, V. A. & Pierce, N. A. ACS Nano 8, 4284-4294 (2014).
28. Larsson, C., Grundberg, I., Soderberg, O. & Nilsson, M. Nat. Methods 7, 395-397 (2010).
29. Chou, C. H. et al. Nucleic Acids Res. 46, D296-D302 (2018).
30. Gadkar, V. J. & Filion, M. A novel method to perform genomic walks using a combination of single strand DNA circularization and rolling circle amplification. J. Microbiol. Methods 87, 38-43 (2011).
31. Serge, A., Bertaux, N., Rigneault, H., Marguet, D., Dynamic multiple target t racing to probe spatiotemporal cartography of cell membranes. Nat. Methods 5, 687-694 (2008).

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the present invention, where the term comprises is used, it is also contemplated that the embodiments consist essentially of, or consist of, the recited components or steps. Furthermore, the order of steps or the order for performing certain actions is immaterial as long as the invention remains operable. Moreover, two or more steps or actions can be conducted simultaneously.

In the specification, singular forms also include plural forms, unless the context clearly dictates otherwise. Unless defined otherwise, all technical and scientific terms used herein have the same meaning as commonly understood by one of ordinary skill in the art to which this invention belongs. In the case of conflict, the present specification will control. Furthermore, it should be recognized that in certain instances a composition can be described as being composed of the components prior to mixing, because upon mixing certain components can further react or be transformed into additional materials.

All percentages and ratios used herein, unless otherwise indicated, are by weight.

What is claimed is:

1. A system for quantifying nucleic acid at a single molecule level in a biological sample, the system comprising:
   (1) a sub-system for extending the nucleic acid to form an amplicon,
   (2) a subsystem for labeling the amplicon with more than one fluorescent dye to form a labeled nucleic acid amplicon, wherein the labeled nucleic acid amplicon is labeled by:
      (i) hybridization of the nucleic acid amplicon with a fluorescent dye conjugated to a single-stranded nucleic acid or nucleic acid analog,
      (ii) binding or intercalation of single-stranded nucleic acid-specific or double-stranded nucleic acid-specific fluorescent dyes with the amplicon, and/or
      (iii) addition of the fluorescent dye into the nucleic acid amplicon by enzymatic incorporation of a fluorescent dye labeled nucleoside triphosphate or deoxyribonucleoside 5'-triphosphate,
   (3) a fluorescence detection sub-system comprising an excitation source and fluorescence detector for excitation of the fluorescently labeled amplicon and measuring fluorescence emission from individual molecules of the fluorescently labeled amplicon, wherein the excitation source comprises a laser source, an incandescent light source, or an light emitting light source, and
   (4) software to record and analyze the fluorescence emission from the detection subsystem wherein the software to record and analyze the fluorescence emission facilitates minimizing or eliminating aberrant counts from the fluorescence emission of the fluorescently labeled single-stranded DNA amplicon by correlating signals from multiple fluorescent labels with optical scattering events using multiparametric gating.

2. The system according to claim 1 wherein extending the nucleic acid is facilitated by enzymatic amplification of the nucleic acid by rolling circle amplification.

3. The system according to claim 1 wherein the excitation source comprises a laser.

4. The system according to claim 1 wherein the fluorescence detection sub-system comprises a microfluidic device with multiple optical sensors to measure fluorescence.

5. The system according to claim 1 wherein the fluorescence detection sub-system comprises a flow cytometer.

6. The system according to claim 1 wherein the amplicon comprises double-stranded DNA, single-stranded DNA, single-stranded RNA or a concatemer of RNA and DNA.

7. The system according to claim 1 wherein the fluorescent dye-conjugated single-stranded nucleic acid comprises primarily single-stranded DNA, single-stranded RNA, single-stranded peptide nucleic acid (PNA) or single-stranded locked nucleic acid (LNA).

8. The system according to claim 1 wherein the fluorescent dye-conjugated single-stranded nucleic acid comprises as a fluorescent dye, one or more light emitting coumarin, cyanine, fluorescein, rhodamine, oxazine, Alexa, ATTO, or BODIPY, fluorescent phycobiliprotein, green fluorescent protein, DsRed dye, light-emitting semiconductor nanocrystal, or light-emitting organic polymer, nanoparticle, or bead.

9. The system according to claim 1 wherein the target nucleic acid for quantitation is double-stranded DNA, single-stranded DNA, micro RNA (miRNA), messenger RNA (mRNA), long non-coding RNA (lncRNA), ribosomal RNA (rRNA), transfer RNA (tRNA), small nuclear RNA (snRNA), small nucleolar RNA (snoRNA), Piwi-interacting RNA (piRNA), interfering RNA (siRNA), antisense RNA (aRNA), transfer messenger RNA (tmRNA), tRNA-derived small RNA (tsRNA), rDNA-derived small RNA (srRNA), ribozyme, viral RNA or double-stranded RNA.

10. The system according to claim 9 further comprising a categorizing sub-system for spectrally barcoding the fluorescently labeled single-stranded DNA amplicon to multiplex numerous miRNA sequences.

11. The system according to claim 10 wherein the spectral barcoding is performed using designed template sequences, which result in the generation of complementary amplicons sequences that can be fluorescently labeled in a sequence specific manner.

12. The system according to claim 10 wherein fluorescence labeling results from sequence specific incorporation of fluorescent dye labeled nucleoside triphosphate or deoxyribonucleoside 5'-triphosphate.

13. The system according to claim 10 wherein the spectral barcoding is accomplished using multiparametric single-molecule analysis.

14. The system according to claim 10 wherein the spectral barcodes are differentiated using, at least in part, data from colorimetric and/or ratiometric selections.

15. The system according to claim 1 wherein the more than one fluorescent dye comprises one or more intercalating fluorescent dyes that exhibit a fluorescence enhancement of at least 10 times upon binding of the intercalating fluorescent dye to double-stranded DNA.

16. A system according to claim 15 wherein the one or more intercalating fluorescent dyes comprises one or more cyanine dyes.

* * * * *